United States Patent [19]

Beineke

[11] Plant 4,614

[45] Jan. 6, 1981

[54] DISTINCT VARIETY OF BLACK WALNUT TREE

[75] Inventor: Walter F. Beineke, West Lafayette, Ind.

[73] Assignee: Purdue Research Foundation, West Lafayette, Ind.

[21] Appl. No.: 939,833

[22] Filed: Sep. 5, 1978

[51] Int. Cl.[2] ..... A01H 5/00

[52] U.S. Cl. ..... Plt./32

[58] Field of Search ..... Plt./32

*Primary Examiner*—Robert E. Bagwill
*Assistant Examiner*—James R. Feyrer
*Attorney, Agent, or Firm*—John R. Nesbitt

[57] ABSTRACT

A new and distinct variety of black walnut tree (*Juglans nigra L.*) which is characterized by rapid growth rate, strong central stem tendency, and outstanding straightness for timber purposes. The nut-bearing habits of this tree are inferior. The pistillate flowers mature very late while pollen maturity is fairly late. In most years there is no overlap in female and male flowering. Flowering begins very late in the life of the tree. The nuts are large and ripen in mid-season. Nut crops occur rarely and are very light. This new cultivar of black walnut tree was discovered by the applicant in Carroll County near Camden, Ind., in a cultivated area. It occurred as a wild tree growing on land managed for timber-growing purposes and was discovered in the course of a search for unique and high quality black walnut trees to be utilized in breeding for outstanding timber qualities. The original tree was cut and sold for high quality veneer. This selection has been designated as BW68 in records maintained on the performance of grafts made from the original selection at Purdue University and will be known henceforth as "Purdue 2".

2 Drawing Figures

DESCRIPTION OF THE DRAWINGS

FIGS. 1 and 2 are photographic reproductions in color of the tree showing its timber form.

BACKGROUND OF THE INVENTION

The aforesaid tree was reproduced by collecting scions from the original clone selection and grafting these onto common black walnut rootstocks at Martell Forest, Purdue University. These asexual reproductions ran true to the parent tree and to each other in all respects.

DETAILED DESCRIPTION OF THE NEW VARIETY

The botanical details of this new and distinct variety of walnut tree are as follows:

Tree:
- *Size.*—Large.
- *Vigor.*—Vigorous.
- *Growth rate.*—Rapid growth — 22% larger in diameter than average, 27% taller in height than average, and 57% more cubic foot volume than average at 7 years of 16 clones.
- *Form.*—Excellent timber form — 39% straighter than average. Strong central stem tendency and narrow crown development.

Trunk:
- *Bark.*—Dark brown to gray.
- *Texture.*—Interlacing ridges.

Branches:
- *Diameter.*—Smaller than average.
- *Length.*—Shorter than average.
- *Branch angle.*—Lower branches — 66° — about average.

Foliage:
- *Quantity.*—Abundant.
- *Density.*—Heavy.

Leaves:
- *Compound leaves.*—Size — average; average length 16".
- *Leaflets.*—Size — medium; average length — $3\frac{3}{4}$"; average width — $1\frac{1}{4}$".
- *Shape.*—Lanceolate; acutely pointed. Thickness — thin.
- *Texture.*—Smooth; margin — serrated; petiole — short; color — topside — dark green; underside — light green.
- *Anthracnose resistance.*—Fair resistance — 9% better than average.
- *Time of leafing.*—Late — averages 9 days later or 75% later than average.

Flowering habit:
- *Age at which tree starts producing catkins.*—Late — 5 years.
- *Number of catkins produced.*—Few.
- *Size of catkins.*—Average.
- *Time of pollen shed.*—Late.
- *Age at which time tree starts producing pistillate flowers.*—Late — 5 years.
- *Number of pistillate flowers produced by young trees.*—Very few.
- *Number of pistillate flowers produced by mature tree.*—Unknown.
- *Lateral shoots producing pistillate flowers.*—None.
- *Number of pistillate flowers per inflorescence.*—Average 2.0.
- *Timing of pistillate flower receptivity.*—Very late.
- *Coincidence of staminate and pistillate bloom.*—Totally separate.

Nut crop:
- *Bearing.*—Rare.
- *Productivity.*—Very light to none.
- *Ripening period.*—Mid season.
- *Evenness of maturity.*—Unknown.
- *Quality.*—Unknown.
- *Distribution of nuts on tree.*—Unknown.

Hull:

*Outer surface.*—Smooth to slight wartiness.

*Form.*—Pointed basal end.

*Thickness.*—Thick.

*Size.*—Large; average length — $2\frac{1}{2}''$; average diameter in suture plane — $1\frac{5}{8}''$; average diameter cheek to cheek — $1\frac{3}{4}''$.

Nut:

*Size.*—Medium; average length — $1\frac{1}{2}''$; average diameter in suture plane — $1\frac{1}{8}''$.

*Uniformity of size.*—Little variation.

*Form.*—Round.

*Blossom end.*—Flattened or rounded.

*Basal end.*—Slightly pointed.

*The amount of nut meat to kernal.*—19%.

The walnut tree and its nuts herein described may vary in slight detail due to climatic and soil conditions under which the variety may be grown; the present description being of the variety as grown near West Lafayette, Ind.

What is claimed is:

1. A new and distinct variety of black walnut tree substantially as illustrated and described, which has excellent timber quality, is fast growing, has strong central stem tendency, little sweep, few crooks; late in time of leafing, pistillate flowers very late, pollen sheds late, and a nut crop is seldom produced.

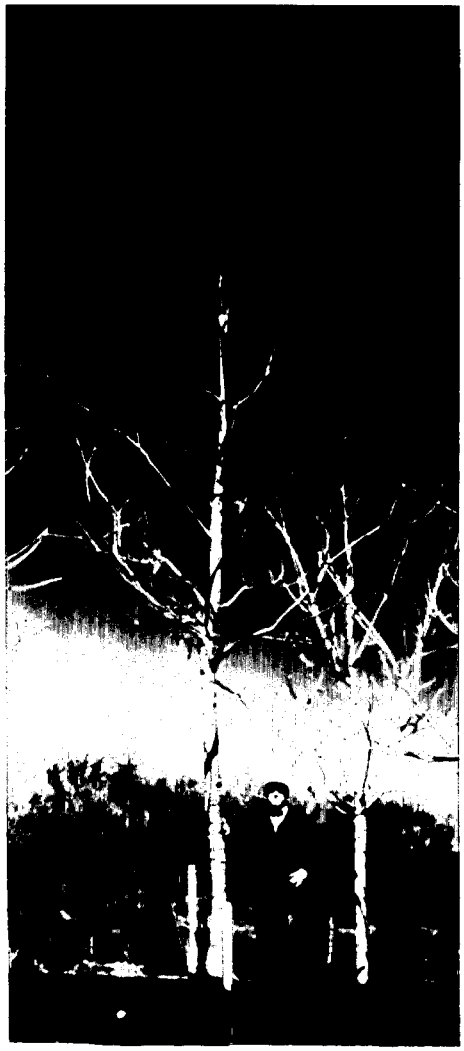
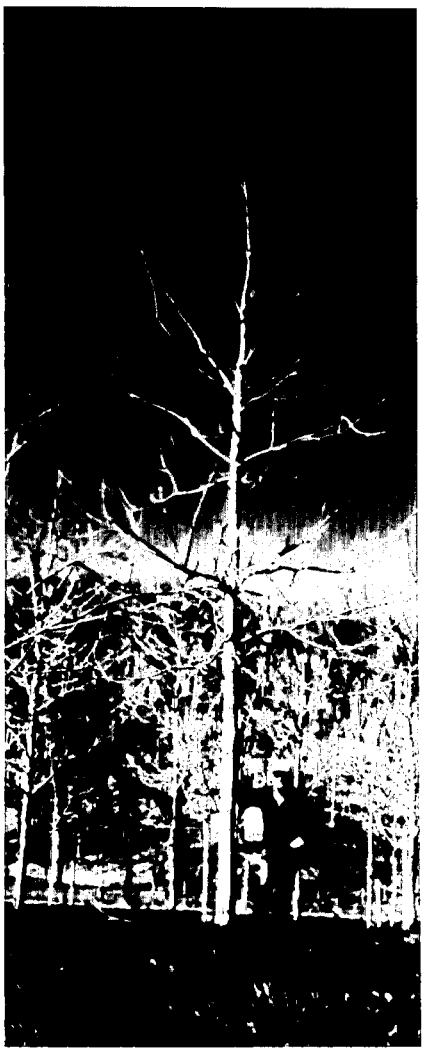

* * * * *